(12) United States Patent
Tyrrell

(10) Patent No.: US 6,435,188 B2
(45) Date of Patent: Aug. 20, 2002

(54) PATIENT IMMOBILIZATION SYSTEM

(76) Inventor: Martin G. Tyrrell, 841 Crescent St., E. Brgdwtr, MA (US) 02333-1609

( * ) Notice: Subject to any disclaimer, the term of this patent is extended or adjusted under 35 U.S.C. 154(b) by 0 days.

(21) Appl. No.: 09/901,842

(22) Filed: Jul. 9, 2001

Related U.S. Application Data

(60) Provisional application No. 60/217,117, filed on Jul. 10, 2000.

(51) Int. Cl.[7] .................................................. A61F 5/37
(52) U.S. Cl. ................................ 128/870; 5/624; 5/625
(58) Field of Search ............................... 128/845, 846, 128/869, 870; 5/624, 625, 628

(56) References Cited

U.S. PATENT DOCUMENTS

| | | | | |
|---|---|---|---|---|
| 3,707,734 A | * | 1/1973 | Matthews | 5/81 |
| 4,369,982 A | * | 1/1983 | Hein | 128/870 |
| 5,435,323 A | * | 7/1995 | Rudy | 128/870 |
| 6,244,270 B1 | * | 6/2001 | Lutian | 128/869 |

* cited by examiner

Primary Examiner—Michael A. Brown
(74) Attorney, Agent, or Firm—John P. McGonagle

(57) ABSTRACT

A backboard having mounting members disposed along the board side edges. The invention provides a number of adjustable straps adapted to being releasably attached to the mounting members. One strap is extended over a patient's lower extremities and attached to the mounting members on each side of the patient. Another strap is positioned over the forehead of a patient and attached to mounting members on each side of the patient's head. Another strap is positioned over the chin area of a patient and attached to mounting members on each side of the patient's head. The chin strap mounting members are positioned closer to the board top than the forehead strap mounting members.

10 Claims, 3 Drawing Sheets

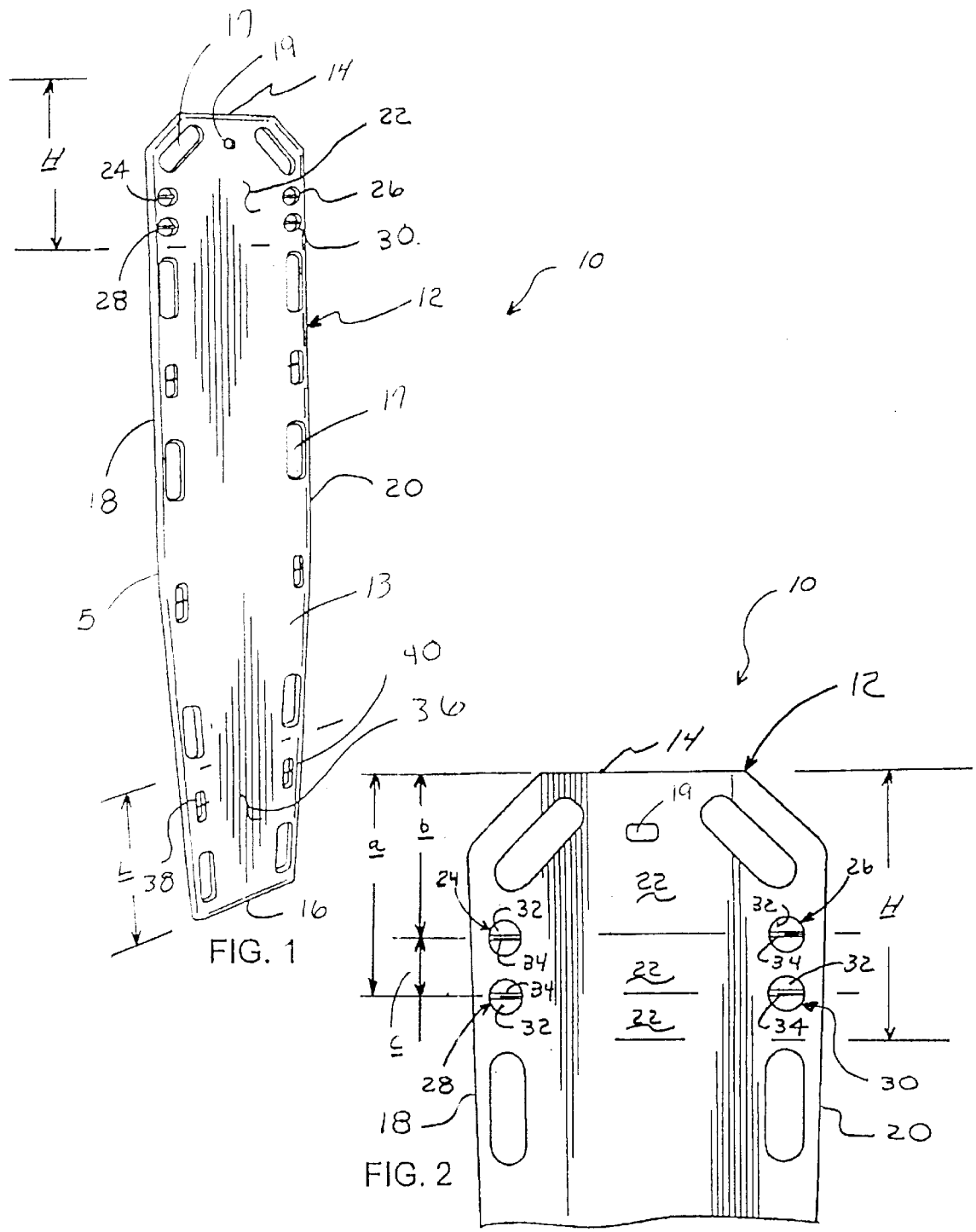

PATIENT IMMOBILIZATION SYSTEM

This application claims benefit to Provisional Application No. 60/217,117 filed Jul. 10, 2000.

BACKGROUND OF THE INVENTION

This invention relates to spinal backboards, and more particularly to a novel system for immobilizing a person's head on a spinal backboard.

Emergency Medical Technicians (EMTs) are often required to treat persons who have sustained possible spinal injuries. In such cases it is very important for the EMTs to immobilize the spinal column of the injured person in order to prevent further injury during treatment and transportation. All too often, however, the immobilization engaged by the EMTs is merely an illusion of spinal stabilization. Conventional devices used to immobilize a person consist of a spine board and various means with which to secure the patient's body and head. The person's body is typically fastened to the spine board (or backboard) by using seatbelt-style straps. The body straps usually connect to the backboard by using clips, which snap onto recessed pins, or by wrapping around various handhold slots and connecting back to themselves. The straps are then tightened to secure the person to the backboard. Three body straps are standard for each patient with straps placed at the chest, pelvis, and knees. The straps may be placed parallel to each other or they may crisscross over the patient to ensure stabilization. Another aspect of the spinal immobilization process is the immobilization of the injured person's head. Although this is the next step after securing the body, the head is always treated as a separate entity entirely. Once immobilized to a backboard, patients must be moved to the awaiting ambulance and then to a hospital gurney. Occasionally, patients must be rolled onto their sides. This is usually due to the patient being pregnant or due to airway maintenance issues such as active vomiting or excessive oral bleeding. Commonly, adhesive tape or Velcro straps are utilized during the immobilization process. Other devices such as cardboard head pads are also used by some EMTs when immobilizing a person's head. Such devices have numerous drawbacks.

Although emergency medical services (EMS) have been in existence in its modern form for approximately thirty years, spinal immobilization, more specifically cervical spinal immobilization, has essentially remained the same. The immobilization techniques and devices currently being utilized by most EMTs have pronounced limitations.

In that most spinal injuries are the result of motor vehicles accidents, EMT's often treat the injured person outdoors and in severe weather environments such as rain and/or snow. In such environments, the spine board becomes wet and/or otherwise contaminated and adhesive tape, which is used by many EMS agencies, may not securely immobilize the injured person's head. Furthermore, it takes a great deal of time to apply the adhesive tape to the person's head and around a spine board. One person must maintain in-line stabilization of the injured person's head while another EMT lifts the head end of the backboard. While the backboard is held up, a third EMT can apply the adhesive tape to the head and around the backboard. Although the adhesive tape may be secured appropriately, the integrity of immobilization is easily breached. Adhesive tape has a tendency to loosen with even the slightest shift in weight, whether during extrication from a second floor apartment or from the patient merely moving about. A person with an altered level of consciousness or head injury can easily dislodge the tape or remove it entirely without much effort. The adhesive tape is also ineffective when a person must be placed on his or her side. When a person who has been immobilized with the use of tape is turned onto his side, his head will always move laterally causing possible exacerbation of an existing injury. Even when adhesive tape is effective in securing a person's head, the tape will almost always become entangled in the person's hair causing further distress to the person. The adhesive tape also leaves residue on the backboard, which must be scrubbed to rid the device of potential pathogens or other disease causing agents.

Hook and loop fastener straps, commonly referred to under the trademark, Velcro, while more quickly applied, have their own inherent deficiencies. Hook and loop straps need loops to be applied to the spine board through which the straps can be fastened. This has, in the past, been accomplished by pre-loading spine boards with pads that have plastic loops incorporated into their design. By pre-loading pads, pre-hospital care providers almost assuredly provided areas in which pathogens could survive. Additionally, Velcro and other hook and loop fasteners have a tendency to retain blood, tissue, and other foreign matter. This retention quality is best demonstrated by pouring hydrogen peroxide over Velcro straps which have been in service for any length of time. Even the most thorough cleaning will usually reveal some hidden blood. This is a major cross-contamination issue, which has not yet been adequately addressed by the pre-hospital provider community. Another problem with Velcro is that hook and loop fasteners are easily removed by a patient with an altered level of consciousness or head injury. Additionally, because the hook and loop fasteners are not secured directly to the backboard, there is some 'play' inherent to the device. A person who has been immobilized with the use of hook and loop fasteners will slide laterally when the backboard is turned onto its side. This lateral movement compromises the entire immobilization and may further injure the person.

Cardboard head immobilizers are occasionally used to secure an injured person's head to a backboard. These devices are an inexpensive alternative to taping the person to the backboard. These cardboard devices, while offering more stabilization than tape alone, must still use adhesive to be secured to the backboard. Because of the use of adhesive, the cardboard immobilizers are dependent upon weather conditions, essentially making the device ineffective in wet or cold environments. The cardboard, while fluid resistant, may break down in adverse environments, such as during a heavy downpour, rendering the immobilizer ineffective. When these devices are secure to a person's head by the use of tape or hook and loop fasteners, the problems associated with the use of Velcro as described above arise. Cardboard immobilizers, while inexpensive, are single use only. There is no way to clean the cardboard. Also, a patient with an altered level of consciousness or a head injury can easily remove the cardboard device. Additionally, the cardboard immobilizers offer little or no stability when the patient is placed on his or her side, thereby compromising the integrity of the immobilization.

While creating a design that would benefit the field of Emergency Medical Services, Applicant addressed the issue of spinal immobilization. More specifically, Applicant concentrated on the immobilization of a person's head to a rigid spine board. Applicant set some parameters within which the design would focus. Spinal immobilization should be consistent regardless of the environment in which the procedure is performed. A person involved in a motor vehicle accident during a downpour at night should expect the same level of care as rendered to the person who fell on a warm, sunny day. Procedures used to provide pre-hospital care should not involve the risk of contaminating a patient with pathogens acquired from previous patients, as is often the case with hook and loop fasteners. Additionally, procedures utilized to render care should be quick and efficient so as to create the least amount of discomfort to the patient as possible with the least amount of manipulation. Once the patient has been immobilized, the integrity of the immobilization must be maintained even when manipulation of the backboard is necessary, such as when a person has to be moved from one floor level to another. When circumstances arise that call for the placement of the backboard on its side such as for pregnant women or for vomiting patients, lateral movement should be eliminated. Head blocks used to stabilize a person's head should be reusable, but easily replaced if contaminated. Individual members of the immobilization system should be easily cleaned with the use of currently accepted chemicals. Head blocks should have holes incorporated into their design so that the ears can be easily monitored for blood, cerebrospinal fluid, or other matter. By incorporating ear holes into head blocks, the patient's ability to hear is maintained making the entire immobilization process less anxiety producing. When a patient has an altered level of consciousness, he or she should not be able to easily compromise the integrity of the immobilization. Furthermore, the person's head should be essentially locked into place to prevent possible movement of an injury. This 'locking in place' of the head can be achieved by crisscrossing the head straps. By crisscrossing the head straps, the patient is less able to thrust his or her chin or forehead outward. Other systems allow for this movement, but movement of the cervical vertebrae just 3 millimeters in the wrong direction can cause permanent damage or even death.

There were many other considerations taken into account during the design of the present invention head immobilization system. The system should above all be effective while still being easy to use. Straps, which immobilize the head, should integrate with the backboard itself without the use of intermediary members. By eliminating intermediate connecting devices, such as preloaded pads, a more effective immobilization can be attained. The use of adhesive and hook and loop fasteners were not considered because of the aforementioned inherent problems with each. The system should have the ability to be incorporated into a variety of backboards modified to receive the head strap members while maintaining the spirit of the design. The head straps themselves should be easily adjusted to secure the patient quickly and efficiently. The head immobilization system should also be able to utilize a variety of head blocks while still being true to the design. For example, during a multiple casualty incident rolled towels or blankets can be used while maintaining the integrity of the system as a whole. The system should also be X-ray transparent to allow continuity of care once the patient has been delivered to a hospital setting. By being X-ray transparent and free of metal pieces, the patient can undergo X-rays, CT scans, and MRIs without having to remove the immobilization.

SUMMARY OF THE INVENTION

The present invention is a system for immobilizing an injured person. More specifically, the invention concentrates on the immobilization of an injured person's head. In one embodiment, the invention is comprised of a backboard having a top edge, a bottom edge, first and second side edges, a head portion and a leg portion. The head portion is comprised of first and second mounting members disposed near the first and second side edges, respectively. Each of the first and second mounting members has a mounting pin. The invention is further comprised of a head block member disposed upon said head portion. The system invention is further comprised of a first head strap member consisting of a first end having a first clip member and a second end having a second clip member. The first and second clip members are engaged with the first and second mounting members of the head portion, respectively, to secure the person's head within the head blocks and to the backboard member thereby immobilizing the head of the person. The combination of the quick connect mounting members and quick connect head straps allow EMTs to quickly immobilize an injured person's head. Such immobilization can be achieved during all types of outdoor environments. Furthermore, the invention is reusable and can easily be disinfected.

These together with other objects of the invention, along with various features of novelty which characterize the invention, are pointed out with particularity in the claims annexed hereto and forming a part of the disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

FIG. 1 is a perspective view of the backboard without straps;

FIG. 2 is a top plan view of the head portion of the backboard shown in FIG. 1;

DETAILED DESCRIPTION OF THE INVENTION

Figure 3:
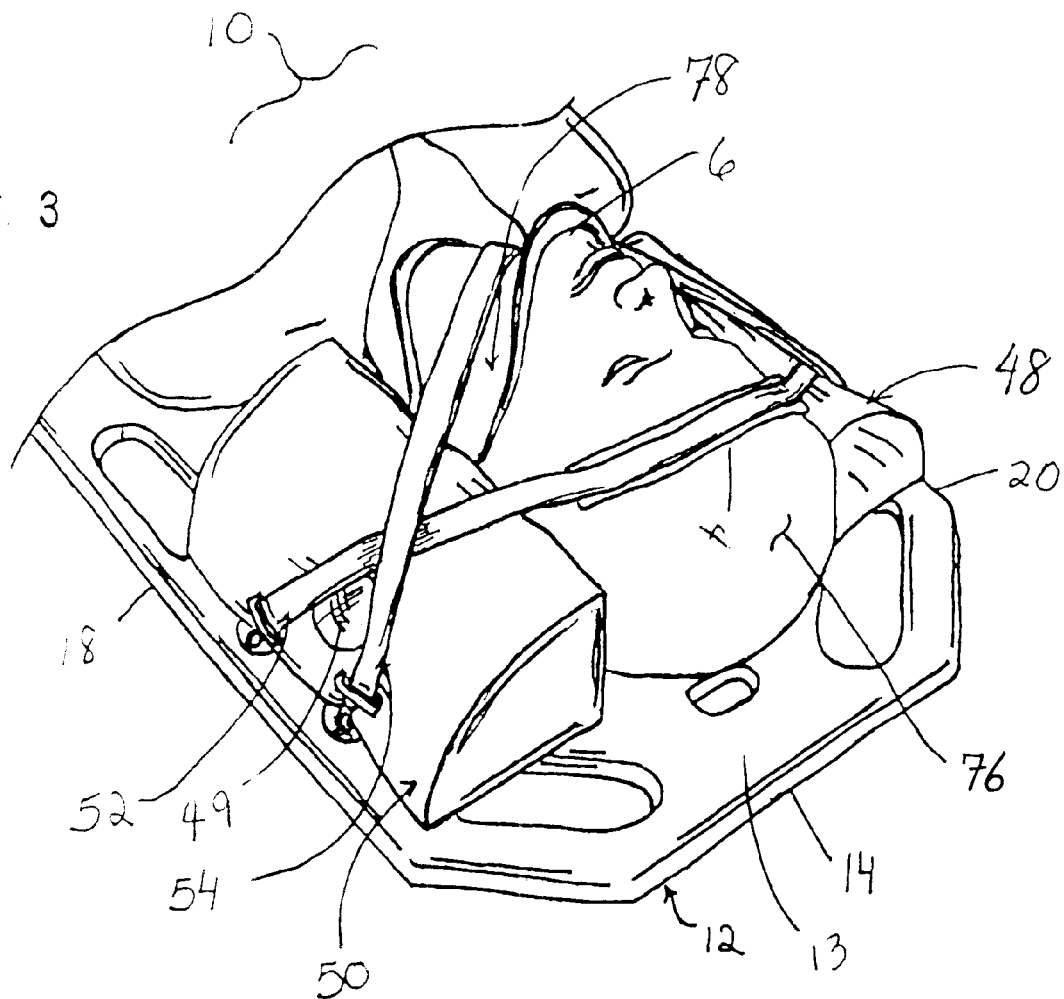
FIG. 3 is a perspective view of the head portion of the invention with a patient.

Referring to the drawings in detail wherein like elements are indicated by like numerals, there is shown a patient immobilization system 10 comprised of a generally flat backboard 12 having a top edge 14, a bottom edge 16, a first side edge 18, a second side edge 20, a head portion 22, and a leg portion 36. The backboard 12 has two surfaces, an upper patient surface 13 and an opposite under surface 15. The backboard top edge 14 and bottom edge 16 define a backboard longitudinal axis. The head portion 22 extends along the backboard 12 a longitudinal distance H from the top edge 14. In this embodiment, the distance H is in the range of ten to eighteen inches. The head portion 22 provides an area in which to immobilize the head of an injured person.

The head portion 22 is typically used in conjunction with a head block disposed upon said head portion 22, said head block comprised generally of two block members 48, 50 positioned laterally about a patient's head 76. The head blocks 48, 50 are composed of material suited for repeated use with consecutive patients. The head blocks could also be made as a single-use, throw-away item. In this embodiment of the invention the head blocks 48, 50 have a quarter-round cross-section transverse to a longitudinal axis coincident with the longitudinal axis of the backboard 12. Each head block 48, 50 has a cylindrical aperture 49 formed therein perpendicular to the backboard upper surface 13 and transverse to the head block longitudinal axis. The head block apertures 49 permit access to a patient's ears thereby enabling increased patient care by creating an area to check for blood and/or cerebrospinal fluid and/or other clinical abnormalities.

The backboard 12 has a plurality of typical hand-hold apertures 17 along the edges 14, 16, 18, 20 for backboard manipulation by EMTs, as well as a central hole 19 in the head portion 22 for engagement with a pull strap (not shown). The backboard 12 is composed of sealed wood or plastic or similar materials so as to be impervious to fluids, thereby allowing repeated cleaning with harsh chemicals and the like to remove possible pathogens after use.

The head portion 22 is generally comprised of a first quick connect mounting member 24, a second quick connect mounting member 26, a third quick connect mounting member 28, and a fourth quick connect mounting member 30. The first and third quick connect mounting members 24 and 28 are positioned along the first side edge 18 while the second and fourth quick connect mounting members 26 and 30 are positioned along the second side edge 20. The centerlines of the first and second quick connect mounting members 24 and 26 are coincident with the longitudinal axis of the backboard and are positioned a longitudinal distance b from the top edge 14. In the embodiment shown, the distance b is in the range of five to eighteen inches. The centerlines of the third and fourth quick connect mounting members 28 and 30 are coincident with the longitudinal axis of the backboard and are positioned a longitudinal distance a from the top edge 14. In the embodiment shown, the distance a is in the range of five to eighteen inches. The first and second quick connect mounting members 24 and 26 are spaced a distance c from the third and fourth quick connect mounting members 28 and 30. In this embodiment of the invention each of the quick connect mounting members 24, 26, 28, and 30 are comprised of a recess 32 and a pin 34 or mounting surface mounted therein, said recess extending through the backboard 12 and opening out through both surfaces 13, 15. Each pin 34 is adapted to engage quick connect straps 52 and 54 described below. In the embodiment shown, each recess 32 has a circular shape and each is large enough to allow the quick connect straps 52 and 54 to engage the pin 34. In the embodiment shown, the pin 34 is of cylindrical shape, however, it may take a variety of other shapes. The mounting members could also be anchoring members mounted on the backboard upper surface 13. Although shown as separate members, the first and third mounting members 24 and 28 could also be formed as a single mounting member. Similarly, the second and fourth mounting members 26 and 30 could be formed as a single mounting member. Further, the mounting members 24, 26, 28, and 30 could be disposed above the surface of the backboard 12 rather than formed as a recess therein.

The leg portion 36 extends along the backboard 12 a distance L from the bottom edge 16. The leg portion 36 is generally provided as an area in which to immobilize the lower extremities or legs of an injured person. The leg portion 36 generally is comprised of first and second mounting members 38 and 40 disposed near to the first and second side edges 18 and 20, respectively. The first and second mounting members 38 and 40 are provided so that a strap may be connected thereto to secure the lower extremities of an injured person to the backboard 12. The first and second mounting members 38 and 40 may be of design similar to the quick connect mounting members 24, 26, 28, and 30 of the head portion 22 thereby having a recess 32 and a pin 34 mounted therein.

Figure 4:
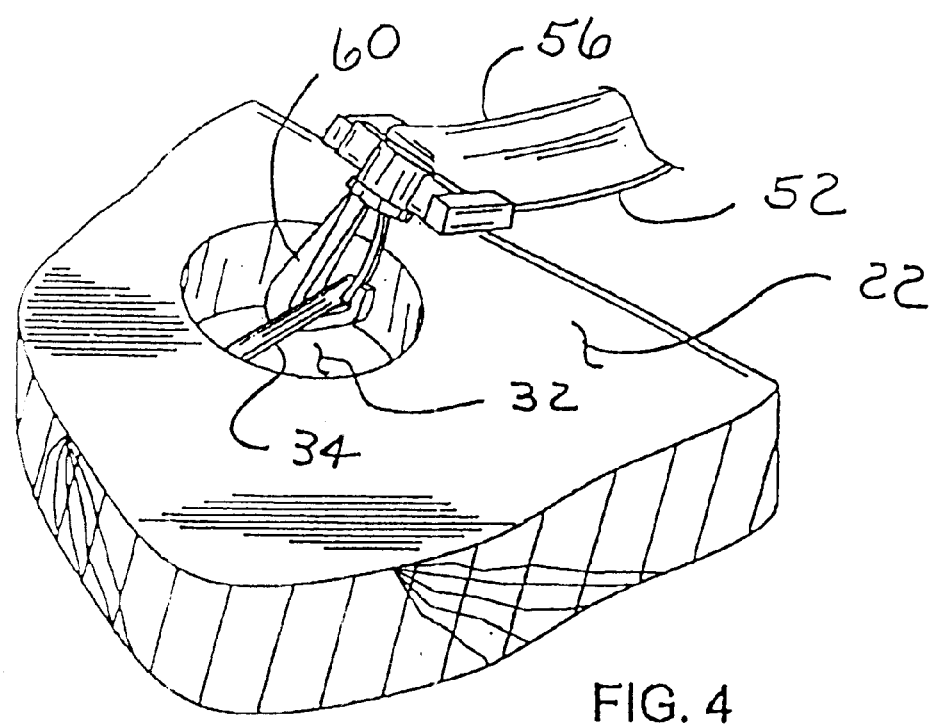
FIG. 4 is a close-up perspective view of a portion of the invention illustrating a quick connect head strap engaged with the quick connect mounting member.
Figure 5:
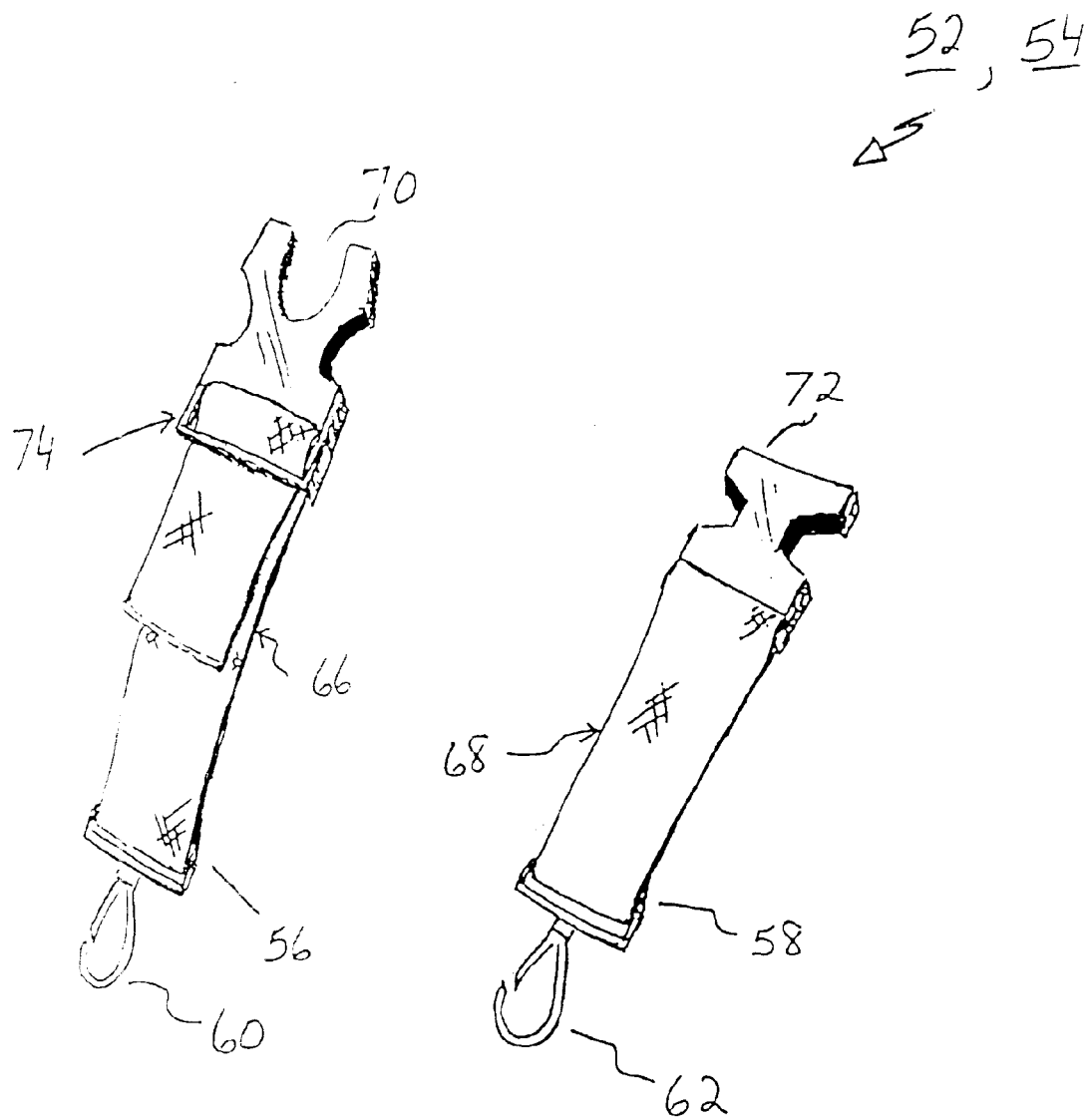
FIG. 5 is a perspective view of the invention quick connect head straps.

The immobilization system 10 is further comprised of first and second quick connect straps 52, 54 which are adapted to allow an EMT to quickly secure a person's head 76 and lower extremities (not shown) to the backboard 12 thereby immobilizing the same. As shown in the figures, especially FIGS. 3–5, each of the first and second quick connect straps 52, 54 have two portions, each portion being comprised of an elongated body 66, 68 with a first end 56, 58 terminating in a clip 60, 62, and a second end terminating in a fastener 70, 72. The first portion fastener 70 is a male plug. The second portion fastener 72 is a female receptacle. The fasteners 70, 72 are adapted to releasably join with each other. The first portion has an adjustment bracket 74 about the body 66 near to the fastener 70, said bracket 74 providing means for adjusting the effective length of the first portion, and thereby the strap 52, 54. The straps 52, 54 are comprised of materials aptly suited for cleaning with the harsh chemicals needed to rid the straps of possible pathogens after strap use, and may be made from nylon webbing, plastic, or other material suited for reuse with consecutive patients. The straps 52, 54 are adapted to be used in conjunction with any type of head block members, including rolled towels and blankets, while maintaining the integrity of the immobilizing system.

The first quick connect head strap 52 is adapted to be engaged with the third and fourth quick connect mounting members 28 and 30 of the head portion 22 and extend upward to secure the forehead area 4 of the person. Specifically, the first portion clip 60 is engaged with the pin 34 of the first quick connect mounting member 28 while the second portion clip 62 is engaged with the pin 34 of the second quick connect mounting member 30. The second quick connect head strap 54 is engaged with the first and second quick connect mounting members 24 and 26 of the head portion 22 and extends downward to secure the chin area 6 of the person. Specifically, the first portion clip 60 is engaged with the pin 34 of the third quick connect mounting member 24 while the second portion clip 62 is engaged with the pin 34 of the fourth quick connect mounting member 26. The first and second quick connect head straps 52 and 54 may take a variety of forms so long as the first end 56 is provided with a clip 60 and a second end 58 is provided with a clip 62. Although shown as two portions, each of the head straps 52 and 54 may be formed as a single piece.

The present invention immobilization system 10 may work in conjunction with a rigid cervical collar 78, which may already be disposed about the person's neck. The cervical collar 78 is generally provided to further immobilize the cervical spine of the person and to provide a means of support to the head strap 54.

When not in use, the system 10 may be stored and/or otherwise transported in a variety of ways. For example, the first quick connect strap 52 may be attached to the head portion 22 by attaching the first clip 60 of the male portion 66 to the first mounting member 24 and the second clip 62 of the female portion 68 to the fourth mounting member 26. Thereafter, the second quick connect head strap 54 may be attached to the head portion 22 by attaching the first clip 60 of the male portion 66 to the third mounting member 28 and the second clip 62 of the female portion 68 to the fourth mounting member 30. The first and second head block members 48 and 50 may be placed next to each other and centrally located on the head portion 22. Thereafter, the male portions 66 of the first and second head straps 52 and 54 may be adjusted such that when secured to their corresponding female portions 68, the head straps 52 and 54 securely fasten the head block members 48 and 50 to the backboard 12. In this orientation, the system 10 may be stored and/or otherwise transported to the site of the injured person.

When use of the system 10 is desired, the male portions 66 and the female portions 68 of head straps 52 and 54 may be disengaged or unmated and the head block members 48 and 50 can be removed. Thereafter, the person may be placed upon the backboard 12 with the person's head 76 disposed about the head portion 22 of the backboard 12. Thereafter, the head block members 48 and 50 may be placed upon both sides of the person's head 76 with the cervical collar 78 already placed about the neck of the person. Thereafter, the length of the male portions 66 of head straps 52 and 54 may be adjusted accordingly and engaged with the female portion 68 such that the first head strap 52 is disposed about the forehead of the person while the second head strap 54 is disposed about the cervical collar 78. After immobilization of the person's body, the patient's head 76 is secured by the straps 52, 54 directly to the backboard 12. The legs of a patient may be secured to the backboard 12 by using one or both straps 52, 54 connected at each end clip 60, 62 to the leg portion mounting members 38, 40. The EMTs may then transport the injured person to the hospital.

It is understood that the above-described embodiment is merely illustrative of the application. Other embodiments may be readily devised by those skilled in the art which will embody the principles of the invention and fall within the spirit and scope thereof.

I claim:

1. A patient immobilization system, comprising:
    a generally flat backboard having a top edge, a bottom edge, a first side edge, a second side edge, an upper patient surface, and an opposite under surface, said top edge and bottom edge defining a backboard longitudinal axis, said backboard having a head portion extending longitudinally a desired distance from said top edge toward said bottom edge, said backboard having a leg portion extending longitudinally a desired distance from said bottom edge toward said top edge, said backboard having a plurality of quick connect mounting members, two of which being positioned in said head portion near said first side edge and two of which being positioned in said head portion near said second side edge, and a number of which being positioned in said leg portion near said first and second side edges; and
    a plurality of quick connect straps, each said strap adapted to releasably engage a quick connect mounting member near said first side edge and a quick connect mounting member near said second edge, said quick connect straps having means for adjusting the length of said strap, two of said quick connect straps each adapted to engage a said head portion quick connect mounting member near said first side edge and a said head portion quick connect mounting member near said second side edge.

2. A patient immobilization system as recited in claim 1, further comprising:
    a head block apparatus disposed upon said backboard head portion, said head block adapted to being positioned laterally about a patient's head.

3. A patient immobilization system as recited in claim 2, wherein:
    said head block apparatus has two apertures formed therein, said apertures adapted to provide access to said patient's ears.

4. A patient immobilization system as recited in claim 3, further comprising:
    a plurality of hand-hold apertures disposed along said backboard edges; and
    a central hole in the said head portion adapted for engagement with a pull strap.

5. A patient immobilization system as recited in claim 4, wherein:
    each said quick connect mounting member is comprised of a recess, said recess extending through the backboard and opening out through both surfaces; and
    a pin mounted within said recess.

6. A patient immobilization system as recited in claim 5, wherein:
    each said quick connect strap has two ends, each said end terminating in a clip adapted to releasably engage said recess pin.

7. A patient immobilization system as recited in claim 6, wherein:
    each said strap is comprised of two portions, each portion being comprised of an elongated body with a first end terminating in said clip and a second end terminating in a fastener, said fastener of one portion adapted to releasably join with the fastener of the other portion, one said portion having an adjustment bracket about the body near to the fastener, said bracket providing means for adjusting the effective length of said portion.

8. A patient immobilization system as recited in claim 7, wherein:
    each said strap is made from a class of materials comprised of plastic, nylon webbing, and materials suited for cleaning with a harsh chemical while maintaining strength for holding a patient immobile.

9. A patient immobilization system as recited in claim 8, wherein:
    said head block apparatus is comprised of two block members positioned laterally about the head of a patient, said head blocks having a quarter-round cross-section transverse to a head block longitudinal axis coincident with the longitudinal axis of the backboard, each block member having an aperture formed therein perpendicular to the backboard upper surface and transverse to the head block longitudinal axis.

10. A method of immobilizing a patient comprising the steps of:
    providing a generally flat backboard having a top edge, a bottom edge, a first side edge, a second side edge, an upper patient surface, and an opposite under surface, said top edge and bottom edge defining a backboard longitudinal axis, said backboard having a head portion extending longitudinally a desired distance from said top edge toward said bottom edge, said backboard having a leg portion extending longitudinally a desired distance from said bottom edge toward said top edge, said backboard having a plurality of quick connect mounting members, two of which being positioned in said head portion near said first side edge and two of which being positioned in said head portion near said second side edge, and a number of which being positioned in said leg portion near said first and second side edges;
    providing a plurality of quick connect straps, each said strap adapted to releasably engage a quick connect mounting member near said first side edge and a quick connect mounting member near said second edge, said quick connect straps having means for adjusting the length of said strap, two of said quick connect straps each adapted to engage a said head portion quick connect mounting member near said first side edge and a said head portion quick connect mounting member near said second side edge;

providing a head block apparatus disposed upon said backboard upper surface on said backboard head portion, said head block apparatus adapted to being positioned laterally about a patient's head, said head block apparatus having two apertures formed therein, said apertures adapted to provide access to said patient's ears;

placing a patient on the backboard upper surface, wherein said patient's head is on the backboard head portion and said patient's legs are on the backboard leg portion;

positioning said head block apparatus about the patient's head and aligning said apertures with the patient's ears;

attaching a cervical collar about the patient, said cervical collar adapted to being engaged by a quick connect strap engaged to a head portion quick connect mounting member;

attaching a first quick connect head strap to a mounting member in the backboard head portion near the board first side;

extending the first strap over the patient's forehead and attaching the other end of the first strap to a mounting member in the board head portion near the board second side;

attaching a second quick connect head strap to a mounting member in the board head portion near the board first side, said mounting member being longitudinally closer to the board top edge than the first strap mounting member;

extending the second strap over the first strap and across the patient's cervical collar back over the first strap and attaching the other end of the second strap to a mounting member in the board head portion adjacent the board second side, said mounting member being longitudinally closer to the board top edge than the first strap mounting member;

attaching a quick connect strap to a mounting member in the board leg portion adjacent the board first side;

extending the strap over the patient's lower extremities and attaching the strap's other end to a mounting member in the board leg portion adjacent the board second side; and adjusting the tension on each strap.

* * * * *